US010779550B2

(12) United States Patent
Chow et al.

(10) Patent No.: US 10,779,550 B2
(45) Date of Patent: Sep. 22, 2020

(54) HUMAN MILK OLIGOSACCHARIDES TO AMELIORATE SYMPTOMS OF STRESS

(71) Applicant: ABBOTT LABORATORIES, Abbott Park, IL (US)

(72) Inventors: Jomay Chow, Westerville, OH (US); Matthew Panasevich, Urbana, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 14/653,480

(22) PCT Filed: Dec. 18, 2013

(86) PCT No.: PCT/US2013/076026
§ 371 (c)(1),
(2) Date: Jun. 18, 2015

(87) PCT Pub. No.: WO2014/100126
PCT Pub. Date: Jun. 26, 2014

(65) Prior Publication Data
US 2015/0320778 A1    Nov. 12, 2015

Related U.S. Application Data

(60) Provisional application No. 61/738,491, filed on Dec. 18, 2012.

(51) Int. Cl.
*A61K 31/7016*    (2006.01)
*A61K 31/702*    (2006.01)
*A23C 9/20*    (2006.01)
*A61K 45/06*    (2006.01)
*A23L 33/00*    (2016.01)

(52) U.S. Cl.
CPC .............. *A23C 9/206* (2013.01); *A23C 9/203* (2013.01); *A23L 33/40* (2016.08); *A61K 31/702* (2013.01); *A61K 31/7016* (2013.01); *A61K 45/06* (2013.01); *A23V 2002/00* (2013.01)

(58) Field of Classification Search
None
See application file for complete search history.

(56) References Cited

U.S. PATENT DOCUMENTS

2007/0104700 A1 * 5/2007 Garcia-Rodenas ........................ A61K 31/202
424/93.45
2008/0124323 A1    5/2008 Boehm et al.
2012/0171165 A1    7/2012 Buck et al.
2012/0172307 A1    7/2012 Davis et al.
2012/0172319 A1    7/2012 Chow et al.
2012/0172330 A1    7/2012 Buck et al.
2013/0150306 A1 *  6/2013 Wittke .................... A61K 38/40
514/17.5

FOREIGN PATENT DOCUMENTS

EP            2708145         3/2014
WO    WO 2012069416 A1 *   5/2012  ............ A23L 1/296
WO         2014/043330       3/2014

OTHER PUBLICATIONS

"Stress" definition in Stedman's Medical Dictionary, website capture http://www.stedmansonline.com/content.aspx?id=mlrS2000011739&termtype=t, retrevied on Apr. 5, 2017.*
Chida, Y., Hamer, M., & Steptoe, A. (2008). A bidirectional relationship between psychosocial factors and atopic disorders: a systematic review and meta-analysis. Psychosomatic Medicine, 70(1), 102-116. (Year: 2008).*
Marques, T. M., Wall, R., Ross, R. P., Fitzgerald, G. F., Ryan, C. A., & Stanton, C. (2010). Programming infant gut microbiota: influence of dietary and environmental factors. Current opinion in biotechnology, 21(2), 149-156. (Year: 2010).*
Arena, M. E., & Manca de Nadra, M. C. (2001). Biogenic amine production by Lactobacillus. Journal of Applied Microbiology, 90(2), 158-162. (Year: 2001).*
"Stress" definition retrieved on Apr. 5, 2017 from http://www.stedmansonline.com (Year: 2017).*
International Search Report and Written Opinion for PCT/US2013/076026 dated Apr. 2, 2014.
Diaz Heijtz et al., "Normal gut microbiota modulates brain development and behavior," Proceedings of the National Academy of Science, vol. 108, No. 7, pp. 3047-3052, Feb. 15, 2011.
Wang et al., "Dietary sialic acid supplementation improves learning and memory in piglets," The American Journal of Clinical Nutrition, vol. 85, No. 2, pp. 561-569, 2007.
Office Action in CA Application No. 2,893,217 dated Aug. 18, 2016.
Office Action in CN Application No. 201380064768.9 dated May 24, 2016.
Office Action in CN Application No. 201380064768.9 dated Jul. 4, 2017.
Examination Report in European Application No. 13818905.5 dated Aug. 17, 2017.

(Continued)

*Primary Examiner* — Dale R Miller

(74) *Attorney, Agent, or Firm* — Calfee, Halter & Griswold LLP

(57)        ABSTRACT

A nutritional composition comprising at least one human milk oligosaccharide selected from 6' sialyllactose, lacto-N-neotetraose, lacto-N-tetraose, disialylated lacto-N-tetraose, 3'-fucosyllactose, and 3'-sialyllactose. The nutritional composition is used in a method of reducing stress in an individual in need thereof.

11 Claims, No Drawings

(56) References Cited

OTHER PUBLICATIONS

Examination Report in Indonesian Application No. P00201503623 dated May 30, 2018 with English Translation.
Exam Report from Malaysian Application No. PI 2015001532 dated May 15, 2018.
Exam Report from Philippine Application No. 1/2015/501309 dated Apr. 26, 2018.
Invitation to Respond to Written Opinion from Singapore Application No. 11201504579Q dated Mar. 26, 2018.
Office Action in CN Application No. 201380064768.9 dated Feb. 3, 2020.
Exam Report from Malaysian Application No. PI 2015001532 dated Feb. 4, 2020.

* cited by examiner

HUMAN MILK OLIGOSACCHARIDES TO AMELIORATE SYMPTOMS OF STRESS

CROSS-REFERENCE TO RELATED APPLICATIONS

This application is the U.S. national phase entry of PCT/US2013/076026, with an international filing date of Dec. 18, 2013, which claims priority to and any benefit of U.S. Provisional Application No. 61/738,491 filed Dec. 18, 2012, the entire contents of which are incorporated by reference in their entirety.

FIELD

The disclosure relates to a nutritional composition for use in a method of reducing stress in an individual in need thereof. More particularly, the nutritional composition comprises at least one human milk oligosaccharide selected from 6'-sialyllactose, lacto-N-neotetraose, lacto-N-tetraose, disialylated lacto-N-tetraose, 3'-fucosyllactose, and 3'-sialyllactose.

BACKGROUND

Infants, children, and adults are often exposed to psychological stress such as changes in social situation (e.g., changes in daycare provider or schools, new family additions, divorce, loss of loved ones, change in career, or job loss). When the stress is extreme, extended exposure may lead to counter-adaptive physiological and behavioral responses such as: anxiety or distress, heightened sensitivity to painful stimuli, depression, and impaired neuronal development or neuronal functioning. Traditional medicine has focused on treating severe symptoms of stress, like depression and anxiety, with pharmaceutical agents such as selective serotonin uptake inhibitors, but these therapies are not suitable for mitigating the effects of milder forms of stress as these compounds can lead to a number of undesirable side-effects. Even more importantly, pharmaceutical interventions may not be appropriate for use in infants and children due to potential side effects on neuronal development. For these reasons, there is a need for non-pharmaceutical interventions that treat, minimize the negative effects of stress, or serve as an adjunctive therapy to pharmaceutical therapeutic agents.

The human gut microbiome exists in symbiosis with its host and it can exert a profound effect on health and disease (Nicholson, 2012). This complex microbial community plays a crucial role in harvesting energy from undigested carbohydrates, promoting maturation of the host immune system, and providing colonization resistance against potential pathogens (Clemente et al., 2012). However, under some conditions, the gut microbiome can also negatively impact human health. Undesirable alterations in the composition of gut microbiota are associated with the development of allergies, Celiac disease, gastric cancer, autism, obesity, anorexia, inflammatory bowel disease (IBD), and type 2 diabetes (Clemente et al., 2012).

Although a growing body of evidence suggests that the composition of the intestinal microbiota alters neuronal development and behavior (Diaz Heijtz et al., 2011), little is known about the relationship between diet, the gut microbiota, and the central and peripheral nervous system. Thus far, it has been shown in animal models that oral administration of certain probiotic bacteria can alter brain lipid composition (Wall et al., 2012), sensitivity to gut pain (Kamiya et al., 2006; Duncker et al., 2011; McKernan et al., 2010), and anxiety-like behavior (Desbonnet et al., 2008). Yet, virtually nothing is known about the interaction between non-digestible dietary carbohydrates, such as human milk oligosaccharides, the intestinal microbiota, and neuronal development and function.

REFERENCES

Clemente J C, Ursell L K, Wegener Parfrey L, et al. The impact of the gut microbiota on human health: an integrative view. Cell 2012; 148:1258-70.

Desbonnet L, Garrett L, Clarke G, et al. The probiotic *Bifidobacteria infantis*: An assessment of potential antidepressant properties in the rat. J Psychiatr Res 2008; 43:164-74.

Diaz Heijtz R, Wang S, Anuar F, et al. Normal gut microbiota modulates brain development and behavior. PNAS 2011; 108:3047-52.

Duncker S C, Kamiya T, Wang L, et al. Probiotic *Lactobacillus reuteri* alleviates the response to gastric distension in rats. J Nutr 2011; 141:1813-18.

Kamiya T, Wang L, Forsythe, P, et al. Inhibitory effects of *Lactobacillus reuteri* on visceral pain induced by colorectal distension in Sprague-Dawley rats. Gut 2006; 55:191-96.

Mckernan D P, Fitzgerald P, Finan T G, et al. The probiotic *Bifidobacterium infantis* 35624 displays visceral antinociceptive effects in the rat. Neurogastroenterol Motil 2010; 22:1029-36

Nicholson J K. Host-gut microbiota metabolic interactions. Science 2012; 336:1262-67.

Wall R, Marques T M, O'Sullivan O, et al. Contrasting effects of *Bifidobacterium breve* NCIMB 702258 and *Bifidobacterium breve* DPC 6330 on the composition of murine brain fatty acids and gut microbiota. Am J Clin Nutr 2012, Vol. 95, p. 1278-87.

BRIEF SUMMARY

A nutritional composition comprising at least one human milk oligosaccharide selected from 6'-sialyllactose, lacto-N-neotetraose, lacto-N-tetraose, disialylated lacto-N-tetraose, 3'-fucosyllactose, and 3'-sialyllactose. The nutritional composition is used in a method of reducing stress in an individual in need thereof.

DETAILED DESCRIPTION

Definitions

The terms "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO" as used herein, unless otherwise specified, refers generally to a number of complex carbohydrates found in human breast milk that can be in acidic or neutral form, and to precursors thereof. Exemplary non-limiting human milk oligosaccharides include 3'-sialyllactose (3SL), 6'-sialyllactose (6SL), lacto-N-neotetraose (LNnT), lacto-N-tetraose (LNT), disialylated lacto-N-tetraose (DSLNT), 3'-fucosyllactose (3FL), and 3'-sialyllactose (3SL), and 2'-fucosyllactose (2FL).

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional composition" as used herein, are used interchangeably and, unless otherwise specified, refer to synthetic formulas including nutritional liquids, nutritional powders, nutritional solids, nutritional semi-solids, nutritional semi-liquids, nutritional supplements, and any other nutritional food product as known in the art. The nutritional powders may be reconstituted to form a nutritional liquid, all of which are suitable for oral consumption by a human. The terms "nutritional formulation" or "nutritional composition" do not include human breast milk.

The term "nutritional liquid" as used herein, unless otherwise specified, refers to nutritional products in ready-to-drink liquid form, concentrated form, and nutritional liquids made by reconstituting the nutritional powders described herein prior to use.

The term "nutritional powder" as used herein, unless otherwise specified, refers to nutritional products in flowable or scoopable form that can be reconstituted with water or another aqueous liquid prior to consumption and includes both spray dried and drymixed/dryblended powders.

The term "nutritional semi-solid," as used herein, unless otherwise specified, refers to nutritional products that are intermediate in properties, such as rigidity, between solids and liquids. Some semi-solids examples include puddings, gelatins, and doughs.

The term "nutritional semi-liquid," as used herein, unless otherwise specified, refers to nutritional products that are intermediate in properties, such as flow properties, between liquids and solids. Some semi-liquids examples include thick shakes and liquid gels.

The term "infant" or "term infant" as used herein, unless otherwise specified, refers to a person 12 months or younger. The term "preterm infant" as used herein, refers to a person born prior to 36 weeks of gestation.

The term "toddler" as used herein, unless otherwise specified, refers to a person greater than one year of age up to three years of age.

The term "child" as used herein, unless otherwise specified, refers to a person greater than three years of age up to twelve years of age.

The term "newborn" as used herein, unless otherwise specified, refers to a person from birth up to four weeks of age.

The terms "infant formula" or "synthetic infant formula" as used herein, unless otherwise specified, are used interchangeably and refer to liquid, solid, semi-solid, and semi-liquid human milk replacements or substitutes that are suitable for consumption by an infant. The synthetic formulas include components that are of semi-purified or purified origin. As used herein, unless otherwise specified, the terms "semi-purified" or "purified" refer to a material that has been prepared by purification of a natural material or by synthesis. The terms "infant formula" or "synthetic infant formula" do not include human breast milk.

The term "synthetic pediatric formula" as used herein, unless otherwise specified, refers to liquid, solid, semi-solid, and semi-liquid human milk replacements or substitutes that are suitable for consumption by an infant or toddler up to the age of 36 months (3 years). The synthetic formulas include components that are of semi-purified or purified origin. As used herein, unless otherwise specified, the terms "semi-purified" or "purified" refer to a material that has been prepared by purification of a natural material or by synthesis. The term "synthetic pediatric nutritional formula" does not include human breast milk.

The term "synthetic child formula" as used herein, unless otherwise specified, refers to liquid, solid, semi-solid, and semi-liquid human milk replacements or substitutes that are suitable for consumption by a child up to the age of 12 years. The synthetic formulas include components that are of semi-purified or purified origin. As used herein, unless otherwise specified, the terms "semi-purified" or "purified" refer to a material that has been prepared by purification of a natural material or by synthesis. The term "synthetic child nutritional formula" does not include human breast milk.

The term "preterm infant formula" as used herein, unless otherwise specified, refers to liquid and solid nutritional products suitable for consumption by a preterm infant.

The term "human milk fortifier" as used herein, unless otherwise specified, refers to liquid and solid nutritional products suitable for mixing with breast milk or preterm infant formula or infant formula for consumption by a preterm or term infant.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

Both γ-Aminobutyric acid (GABA) and agmatine help to reduce stress, anxiety, and hypersensitivity to painful stimuli, and improve mood, relaxation, and calmness. GABA is thought to relieve anxiety, improve mood, reduce symptoms of premenstrual syndrome, treat attention deficit disorder, increase lean muscle mass, promote fat-burning, stabilize blood pressure, and relieve pain, through its action as a primary inhibitory neurotransmitter of the central nervous system. Animal studies indicate that agmatine is a putative neurotransmitter that exhibits antinociceptive, antidepressive, anxiolytic, and neuroprotective properties. Both of these compounds can be absorbed from food or endogenously produced by host cells.

It has been found that GABA and agmatine can be produced in the gut of a human with the already present intestinal flora by feeding particular human milk oligosaccharides (HMO). As shown in tables 1 and 2 and carried out as described in Example 51, anaerobic fermentation cultures of fecal samples taken from either breast-fed infants (BF) or formula-fed infants (FF) and incubated with either lacto-N-neotetraose (LNnT) or 6'-sialyllactose (6'SL) HMOs showed dramatic increases in GABA and agmatine relative to a blank. This in vitro study shows that the consumption of selected HMOs will produce GABA and agmatine in vivo by the human's own intestinal flora.

TABLE 1

Increase of GABA and agmatine in breast fed infants

|  | LNnT/ blank 0 h | LNnT/ blank 3 h | LNnT/ blank 6 h | 6'SL/ blank 0 h | 6'SL/blank 3 h | 6'SL/blank 6 h |
|---|---|---|---|---|---|---|
| GABA | 3.66 | 14.78 | 17.46$^a$ | 1.22 | 3.53 | 5.32 |
| agmatine | 9.52$^a$ | 34.4 | 1.59 | 8.23$^a$ | 10.51 | 3.43 |

$^a$ p ≤ 0.05 and q < 0.10 compared to blank.

TABLE 2

Increase of GABA and agmatine in formula fed infants

|  | LNnT/ blank 0 h | LNnT/ blank 3 h | LNnT/ blank 6 h | 6'SL/ blank 0 h | 6'SL/blank 3 h | 6'SL/blank 6 h |
|---|---|---|---|---|---|---|
| GABA | 3.25 | 27.83$^a$ | 33.42$^a$ | 0.6 | 4.31 | 16.99$^a$ |
| agmatine | 2.12 | 61.77$^a$ | 75.02$^a$ | 1.4 | 11.99 | 3.76 |

$^a$ p ≤ 0.05 and q < 0.10 compared to blank.

The present disclosure provides a nutritional composition comprising at least one human milk oligosaccharide selected from 6'-sialyllactose, lacto-N-neotetraose, lacto-N-tetraose, disialylated lacto-N-tetraose, 3'-fucosyllactose, and 3'-sialyllactose, for use in a method of reducing stress in an individual in need thereof.

Without being bound to a particular theory, it is believed that feeding an individual a nutritional composition comprising at least one of 6'-sialyllactose, lacto-N-neotetraose, lacto-N-tetraose, disialylated lacto-N-tetraose, 3'-fucosyllactose, or 3'-sialyllactose, will result in the intestinal flora consuming these compounds and producing a large increase of GABA, agmatine, or both. The GABA, agmatine, or both will be absorbed through the gut of the individual into their blood stream and then pass through the blood-brain barrier. The GABA, agmatine, or both will then reduce the stress in an individual. Alternatively, the GABA, agmatine, or both may not be required to pass through the blood-brain barrier to have the desirable effect.

Specific non-limiting examples of HMOs that may be included individually or in combination in the compositions used in the method of the present disclosure include: 6'-sialyllactose, lacto-N-neotetraose, lacto-N-tetraose, disialylated lacto-N-tetraose, 3'-fucosyllactose, or 3'-sialyllactose.

In one embodiment, the method of reducing stress in an individual in need thereof comprises administering to the individual a nutritional composition comprising at least one human milk oligosaccharide selected from 6'-sialyllactose and lacto-N-neotetraose. In another embodiment, the nutritional composition comprises lacto-N-neotetraose. In a further embodiment, the nutritional composition comprises 6'-sialyllactose.

In one embodiment, the nutritional composition is a liquid and comprises at least one human milk oligosaccharide selected from 6'-sialyllactose, lacto-N-neotetraose, lacto-N-tetraose, disialylated lacto-N-tetraose, 3'-fucosyllactose, and 3'-sialyllactose, in an amount of from about 0.001 mg/mL to about 20 mg/mL, including from about 0.001 mg/mL to about 10 mg/mL, including from about 0.001 mg/mL to about 5 mg/mL, including from about 0.001 mg/mL to less than about 2 mg/mL, and including from about 0.01 mg/mL to about 20 mg/mL including from about 0.01 mg/mL to less than about 2 mg/mL.

In a specific embodiment, the nutritional composition is a liquid and comprises at least one human milk oligosaccharide selected from 6'-sialyllactose and lacto-N-neotetraose, in an amount of from about 0.001 mg/mL to about 20 mg/mL, including from about 0.001 mg/mL to about 10 mg/mL, including from about 0.001 mg/mL to about 5 mg/mL, including from about 0.001 mg/mL to less than about 2 mg/mL, and including from about 0.01 mg/mL to about 20 mg/mL including from about 0.01 mg/mL to less than about 2 mg/mL.

In a specific embodiment, the nutritional composition is a liquid and comprises 6'-sialyllactose, in an amount of from about 0.001 mg/mL to about 20 mg/mL, including from about 0.001 mg/mL to about 10 mg/mL, including from about 0.001 mg/mL to about 5 mg/mL, including from about 0.001 mg/mL to less than about 2 mg/mL, and including from about 0.01 mg/mL to about 20 mg/mL, including from about 0.01 mg/mL to less than about 2 mg/mL.

In a specific embodiment, the nutritional composition is a liquid and comprises lacto-N-neotetraose, in an amount of from about 0.001 mg/mL to about 20 mg/mL, including from about 0.001 mg/mL to about 10 mg/mL, including from about 0.001 mg/mL to about 5 mg/mL, including from about 0.001 mg/mL to less than about 2 mg/mL, and including from about 0.01 mg/mL to about 20 mg/mL, including from about 0.01 mg/mL to less than about 2 mg/mL.

In one embodiment, the nutritional composition is a powder and comprises at least one human milk oligosaccharide selected from 6'-sialyllactose, lacto-N-neotetraose, lacto-N-tetraose, disialylated lacto-N-tetraose, 3'-fucosyllactose, and 3'-sialyllactose, in an amount of from about 0.0005% to about 5%, such as from about 0.01% to about 1%, by weight of the powder.

In a specific embodiment, the nutritional composition is a powder and comprises at least one human milk oligosaccharide selected from 6'-sialyllactose and lacto-N-neotetraose, in an amount of from about 0.0005% to about 5%, such as from about 0.01% to about 1%, by weight of the powder.

In a specific embodiment, the nutritional composition is a powder and comprises 6'-sialyllactose, in an amount of from about 0.0005% to about 5%, such as from about 0.01% to about 1%, by weight of the powder.

In a specific embodiment, the nutritional composition is a powder and comprises lacto-N-neotetraose, in an amount of from about 0.0005% to about 5%, such as from about 0.01% to about 1%, by weight of the powder.

In a specific embodiment, the nutritional composition is a bar and comprises at least one human milk oligosaccharide selected from 6'-sialyllactose, lacto-N-neotetraose, lacto-N-tetraose, disialylated lacto-N-tetraose, 3'-fucosyllactose, and 3'-sialyllactose, in an amount of from about 0.0005% to about 10%, such as from about 0.01% to about 5%, by weight of the bar.

In a specific embodiment, the nutritional composition is a bar and comprises at least one human milk oligosaccharide selected from 6'-sialyllactose and lacto-N-neotetraose, in an amount of from about 0.0005% to about 10%, such as from about 0.01% to about 5%, by weight of the bar.

In a specific embodiment, the nutritional composition is a bar and comprises 6'-sialyllactose, in an amount of from about 0.0005% to about 10%, such as from about 0.01% to about 5%, by weight of the bar.

In a specific embodiment, the nutritional composition is a bar and comprises lacto-N-neotetraose, in an amount of from about 0.0005% to about 10%, such as from about 0.01% to about 5%, by weight of the bar.

Human Milk Oligosaccharides (HMOs)

Human milk oligosaccharides are one of the main components of human breast milk, which contains, on average, 10 grams per liter of neutral oligosaccharides and 1 gram per liter of acidic oligosaccharides. The composition of human milk oligosaccharides is very complex and more than 200 different oligosaccharide-like structures are known.

The HMOs may be included in the nutritional compositions alone, or in some embodiments, in combination with other immune enhancing factors (e.g., long chain polyunsaturated fatty acids, antioxidants, nucleotides, etc.). The HMO or HMOs may be isolated or enriched from milk(s) secreted by mammals including, but not limited to: human, bovine, ovine, porcine, or caprine species. The HMOs may also be produced via microbial fermentation, enzymatic processes, chemical synthesis, or combinations thereof.

In addition to the HMOs described above, the nutritional compositions disclosed herein may include other HMOs such as: acidic oligosaccharides, neutral oligosaccharides, n-acetylglucosylated oligosaccharides, and HMO precursors. Specific non-limiting examples of HMOs that may be included individually or in combination in the compositions of the present disclosure include: sialic acid (i.e., free sialic acid, lipid-bound sialic acid, protein-bound sialic acid); D-glucose (Glc); D-galactose (Gal); N-acetylglucosamine (GlcNAc); L-fucose (Fuc); fucosyl oligosaccharides (i.e., lacto-N-fucopentaose I; lacto-N-fucopentaose II; 2'-fucosyllactose; 3'-fucosyllactose; lacto-N-fucopentaose III; lacto-N-difucohexaose I; and lactodifucotetraose); non-fucosylated, non-sialylated oligosaccharides (i.e., lacto-N-tetraose and lacto-N-neotetraose); sialyl oligosaccharides (i.e., 3'-sialyl-3-fucosyllactose; disialomonofucosyllacto-N-neohexaose; monofucosylmonosialyllacto-N-octaose (sialyl Lea); sialyllacto-N-fucohexaose II; disialyllacto-N-fucopentaose II; monofucosyldisialyllacto-N-tetraose); and sialyl fucosyl oligosaccharides (i.e., 2'-sialyllactose; 2-sialyllactosamine; 3'-sialyllactose; 3'-sialyllactosamine; 6'-sialyllactose; 6'-sialyllactosamine; sialyllacto-N-neotetraose c; monosialyllacto-N-hexaose; disialyllacto-N-hexaose I; monosialyllacto-N-neohexaose I; monosialyllacto-N-neohexaose II; disialyllacto-N-neohexaose; disialyllacto-N-tetraose; disialyllacto-N-hexaose II; sialyllacto-N-tetraose a; disialyllacto-N-hexaose I; and sialyllacto-N-tetraose b). Also useful are variants in which the glucose (Glc) at the reducing end is replaced by N-acetylglucosamine (e.g., 2'-fucosyl-N-acetylglucosamine (2'FLNac) is such a variant to 2'-fucosyllactose). These HMOs are described more fully in U.S. Patent Application No. 2009/0098240, which is herein incorporated by reference in its entirety. Other suitable examples of HMOs that may be included in the compositions of the present disclosure include lacto-N-fucopentaose V, lacto-N-hexaose, para-lacto-N-hexaose, lacto-N-neohexaose, para-lacto-N-neohexaose, monofucosyllacto-N-hexaose II, isomeric fucosylated lacto-N-hexaose (1), isomeric fucosylated lacto-N-hexaose (3), isomeric fucosylated lacto-N-hexaose (2), difucosyl-para-lacto-N-neohexaose, difucosyl-para-lacto-N-hexaose, difucosyllacto-N-hexaose, lacto-N-neoocataose, para-lacto-N-octanose, iso-lacto-N-octaose, lacto-N-octaose, monofucosyllacto-neoocataose, monofucosyllacto-N-ocataose, difucosyllacto-N-octaose I, difucosyllacto-N-octaose II, difucosyllacto-N-neoocataose II, difucosyllacto-N-neoocataose I, lacto-N-decaose, trifucosyllacto-N-neooctaose, trifucosyllacto-N-octaose, trifucosyl-iso-lacto-N-octaose, lacto-N-difucohexaose II, sialyl-lacto-N-tetraose a, sialyl-lacto-N-tetraose b, sialyl-lacto-N-tetraose c, sialyl-fucosyl-lacto-N-tetraose I, sialyl-fucosyl-lacto-N-tetraose II, and disialyl-lacto-N-tetraose, and combinations thereof. Particularly suitable nutritional compositions include at least one of the following HMOs or HMO precursors: sialic acid (SA); 3'-sialyllactose (3'SL); 6'-sialyllactose (6'SL); 2'-fucosyllactose (2'FL); 3'-fucosyllactose (3'FL); lacto-N-tetraose and lacto-N-neotetraose (LNnT), and in particular, combinations of 6'SL and 3'SL; combinations of 3'FL and SA; combinations of 2'FL and 3'FL; combinations of 2'FL, 3'SL, and 6'SL; combinations of 3'SL, 3'FL, and LNnT; and combinations of 6'SL, 2'FL, and LNnT.

Other exemplary combinations include: SA, 3'SL, 6'SL, 3'FL, 2'FL, and LNnT; 3'SL, 6'SL, 3'FL, 2'FL, and LNnT; SA, 6'SL, 3'FL, 2'FL, and LNnT; SA, 3'SL, 3'FL, 2'FL, and LNnT; SA, 3'SL, 6'SL, 2'FL, and LNnT; SA, 3'SL, 6'SL, 3'FL, and LNnT; SA, 3'SL, 6'SL, 3'FL, and 2'FL; SA and 3'SL; SA and 6'SL; SA and 2'FL; SA and LNnT; SA, 3'SL, and 6'SL; SA, 3'SL and 3'FL; SA, 3'SL and 2'FL; SA, 3'SL and LNnT; SA, 6'SL and 3'FL; SA, 6'SL, and 2'FL; SA, 6'SL, and LNnT; SA, 3'FL, and 2'FL; SA, 3'FL, and LNnT; SA, 2'FL, and LNnT; SA, 3'SL, 6'SL, and 3'FL; SA, 3'SL, 6'SL and 2'FL; SA, 3'SL, 6'SL, and LNnT; SA, 3'SL, 3'FL, and 2'FL; SA, 3'SL, 3'FL, and LNnT; SA, 3'SL, 2'FL, and LNnT; SA, 6'SL, 3'FL, and 2'FL; SA, 6'SL, 2'FL, and LNnT; SA, 6'SL, 3'FL, and LNnT; SA, 3'FL, 2'FL, and LNnT; SA, 6'SL, 2'FL, and LNnT; SA, 6'SL, 2'FL, and LNnT; SA, 3'SL, 3'FL, 2'FL, and LNnT; SA, 6'SL, 3'FL, 2'FL, and LNnT; SA, 3'SL, 6'SL, 3'FL, and LNnT; SA, 3'SL, 3'FL, 2'FL, and LNnT; SA, 3'SL, 6'SL, 2'FL, and LNnT; 3'SL, 6'SL, 3'FL, and 2'FL; 3'SL, 6'SL, 2'FL, and LNnT; 3'SL, 3'FL, 2'FL, and LNnT; 3'SL, 6'SL, 3'FL, and LNnT; 3'SL, 6'SL, and 3'FL; 3'SL, 3'FL, and 2'FL; 3'SL, 2'FL, and LNnT; 3'SL, 6'SL, and 2'FL; 3'SL, 6'SL, and LNnT; 3'SL and 3'FL; 3'SL and 2'FL; 3'SL and LNnT; 6'SL and 3'FL; 6'SL and 2'FL; 6'SL and LNnT; 6'SL, 3'FL, and LNnT; 6'SL, 3'FL, 2'FL, and LNnT; 3'FL, 2'FL, and LNnT; 3'FL and LNnT; and 2'FL and LNnT.

Long Chain Polyunsaturated Fatty Acids (LCPUFAs)

In addition to the HMOs described above, the nutritional composition may include LCPUFAs. LCPUFAs are included in the nutritional compositions to provide nutritional support, as well as to reduce oxidative stress and enhance growth and functional development of the intestinal epithelium and associated immune cell populations. In some embodiments, the nutritional composition includes a combination of one or more HMOs and one or more LCPUFAs such that the composition provides a synergistic benefit to the end user, such as a synergistic benefit in modulating anti-viral immune responses and dampening inflammation.

In some embodiments, the HMO or HMOs used in combination with the LCPUFAs to provide the synergistic effect are acidic HMOs.

Exemplary LCPUFAs for use in the nutritional compositions include, for example, ω-3 LCPUFAs and ω-6 LCPUFAs. Specific LCPUFAs include docosahexaenoic acid (DHA), eicosapentaenoic acid (EPA), docosapentaenoic acid (DPA), arachidonic acid (ARA), linoleic acid, linolenic acid (alpha linolenic acid) and gamma-linolenic acid derived from oil sources such as plant oils, marine plankton, fungal oils, and fish oils. In one particular embodiment, the LCPUFAs are derived from fish oils such as menhaden, salmon, anchovy, cod, halibut, tuna, or herring oil. Particularly preferred LCPUFAs for use in the nutritional compositions with the HMOs include DHA, ARA, EPA, DPA, and combinations thereof.

To reduce potential side effects of high dosages of LCPUFAs in the nutritional compositions, the content of LCPUFAs preferably does not exceed 3% by weight of the total fat content, including below 2% by weight of the total fat content, and including below 1% by weight of the total fat content in the nutritional composition.

The LCPUFA may be provided as free fatty acids, in triglyceride form, in diglyceride form, in monoglyceride form, in phospholipid form, in esterfied form or as a mixture of one or more of the above, preferably in triglyceride form.

The nutritional compositions may comprise total concentrations of LCPUFA of from about 0.01 mM to about 10 mM and including from about 0.01 mM to about 1 mM. Alternatively, the nutritional compositions may comprise total concentrations of LCPUFA of from about 0.001 g/L to about 1 g/L.

In one embodiment, the nutritional compositions include total long chain ω-6 fatty acids in a concentration of from about 100 to about 425 mg/L or from about 12 to about 53 mg per 100 kcals and/or further include total long chain ω-3 fatty acids in a concentration of from about 40 to about 185 mg/L or from about 5 to about 23 mg per 100 kcals. In one specific embodiment, the ratio of long chain ω-6 fatty acids to long chain ω-3 fatty acids in the nutritional compositions ranges from about 2:1 to about 3:1, preferably about 2.5:1.

In one specific embodiment, the nutritional compositions include DHA in a concentration of from about 0.025 mg/mL to about 0.130 mg/mL or from about 3 to about 16 mg per 100 kcals. In another embodiment, the nutritional compositions include ARA in a concentration of from about 0.080 mg/mL to about 0.250 mg/mL or from about 10 to about 31 mg per 100 kcals. In yet another embodiment, the nutritional compositions include combinations of DHA and ARA such that the ratio of DHA to ARA ranges from about 1:4 to about 1:2.

Antioxidants

Additionally, the nutritional compositions may comprise one or more antioxidants in combination with the HMOs (and optionally LCPUFAs and/or nucleotides also) to provide nutritional support, as well as to reduce oxidative stress. In some embodiments, the nutritional composition includes a combination of HMOs and antioxidants such that the composition provides a synergistic benefit to the end user, such as a synergistic benefit in modulating anti-viral immune responses and dampening inflammation. In some embodiments, the HMO or HMOs is used in combination with carotenoids (and specifically lutein, beta-carotene, zeaxanthin and/or lycopene) to provide the synergistic effect.

Any antioxidants suitable for oral administration may be included for use in the nutritional compositions of the present disclosure, including, for example, vitamin A, vitamin E, vitamin C, retinol, tocopherol, and carotenoids, including lutein, beta-carotene, zeaxanthin, and lycopene, and combinations thereof, for example.

The antioxidants for use in the nutritional compositions may be used with the HMOs alone or in combination with HMOs and LCPUFAs and/or nucleotides. In one embodiment, the antioxidants for use in the nutritional compositions include carotenoids. In one embodiment the carotenoids are lutein, lycopene, zeaxanthin and/or beta-carotene. Nutritional compositions containing these combinations, as selected and defined herein, can be used to modulate inflammation and/or levels of C-reactive protein in preterm and term infants.

The nutritional compositions may comprise at least one of lutein, lycopene, zeaxanthin, and beta-carotene to provide a total amount of carotenoid of from about 0.001 µg/mL to about 10 µg/mL. In one embodiment, the nutritional compositions may comprise lutein in an amount of from about 0.001 µg/mL to about 10 µg/mL, including from about 0.044 µg/mL to about 5 µg/mL of lutein, and including from about 0.001 µg/mL to about 5 µg/mL, including from about 0.001 µg/mL to about 0.0190 µg/mL, including from about 0.001 µg/mL to about 0.0140 µg/mL. In another embodiment, the nutritional compositions comprise from about 0.001 µg/mL to about 10 µg/mL, including from about 0.0185 µg/mL to about 5 µg/mL of lycopene, and including from about 0.001 µg/mL to about 5 µg/mL, including from about 0.001 µg/mL to about 0.0130 µg/mL, including from about 0.001 µg/mL to about 0.0075 µg/mL. In another embodiment, the nutritional compositions comprise from about 0.001 µg/mL to about 10 µg/mL of beta-carotene, including from about 0.034 µg/mL to about 5 µg/mL of beta-carotene, including from about 1 µg/mL to about 5 µg/mL, also including from about 0.001 µg/mL to about 0.025 µg/mL, including from about 0.001 µg/mL to about 0.011 µg/mL of beta-carotene. Any combination of these amounts of beta-carotene, lutein, zeaxanthin, and lycopene can be included in the nutritional compositions. Other carotenoids may optionally be included in the nutritional compositions. Any one or all of the carotenoids included in the nutritional compositions may be from a natural source, or artificially synthesized.

Each of the carotenoids in the selected combinations can be obtained from any known or otherwise suitable material source for use in nutritional compositions, and each can be provided individually, or all together, or in any combination and from any number of sources, including sources such as multivitamin premixes containing other vitamins or minerals in combination with one or more of the carotenoids as described herein. Non-limiting examples of some suitable sources of lutein, lycopene, beta-carotene, or combinations thereof include LycoVit® lycopene (available from BASF, Mount Olive, N.J.), Lyc-O-Mato® tomato extract in oil, powder, or bead form (available from LycoRed Corp., Orange, N.J.), beta-carotene, lutein, or lycopene (available from DSM Nutritional Products, Parsippany, N.J.), FloraGLO® lutein (available from Kemin Health, Des Moines, Iowa), Xangold® Natural Lutein Esters (available from Cognis, Cincinnati, Ohio), and Lucarotin® beta-carotene (available from BASF, Mount Olive, N.J).

Nucleotides

In addition to the HMOs, the nutritional compositions may additionally comprise nucleotides and/or nucleotide precursors selected from nucleosides, purine bases, pyrimidine bases, ribose, and deoxyribose. The nucleotide may be in monophosphate, diphosphate, or triphosphate form. The nucleotide may be a ribonucleotide or a deoxyribonucleotide. The nucleotides may be monomeric, dimeric, or polymeric (including RNA and DNA). The nucleotide may be present in the nutritional composition as a free acid or in the form of a salt, preferably a monosodium salt. In some embodiments, the nutritional composition includes a combination of HMOs and nucleotides such that the composition provides a synergistic benefit to the end user, such as a synergistic benefit in modulating anti-viral immune responses and dampening inflammation and/or improving intestinal barrier integrity.

Incorporation of nucleotides in the nutritional compositions of the present disclosure improves intestinal barrier integrity and/or maturation, which is beneficial to preterm and term infants who have less developed intestinal flora and hence a slower maturing intestinal barrier.

Suitable nucleotides and/or nucleosides for use in the nutritional compositions include one or more of cytidine 5'-monophosphate, uridine 5'-monophosphate, adenosine 5'-monophosphate, guanosine 5'-1-monophosphate, and/or inosine 5'-monophosphate, such as cytidine 5'-monophosphate, uridine 5'-monophosphate, adenosine 5'-monophosphate, guanosine 5'-monophosphate, and inosine 5'-monophosphate.

The nucleotides are present in the nutritional compositions in total amounts of nucleotides of at least about 5 mg/L, including at least about 10 mg/L, including from about 10 mg/L to about 200 mg/L, including from about 42 mg/L to about 102 mg/L, and including at least about 72 mg/L of the nutritional product.

In one specific embodiment when the nutritional composition is a nutritional powder, the nucleotide may be present at a level of at least about 0.007%, including from about 0.0078% to about 0.1556%, and including about 0.056% (by weight of the nutritional powder), or at least about 0.007 grams, including from about 0.0078 grams to about 0.1556 grams, and including about 0.056 grams of nucleotide per 100 grams of nutritional powder.

In another specific embodiment, when the nutritional composition is a ready-to-feed nutritional liquid, the nucleotide is present at a level of at least about 0.001%, including from about 0.001% to about 0.0197%, and including about 0.0071% (by weight of the nutritional liquid), or at least about 0.001 grams, including from about 0.001 grams to about 0.0197 grams, and including about 0.0071 grams of nucleotide per 100 grams of ready-to-feed nutritional liquid.

In another specific embodiment when the nutritional composition is a concentrated nutritional liquid, the nucleotide is present at a level of at least about 0.0019%, including from about 0.0019% to about 0.0382%, and including about 0.0138% (by weight of the nutritional liquid), or at least about 0.0019 grams, including from about 0.0019 grams to about 0.0382 grams, and including about 0.0138 grams of nucleotide per 100 grams of concentrated nutritional liquid.

Macronutrients

The nutritional compositions may be formulated to include at least one of protein, fat, and carbohydrate. In many embodiments, the nutritional compositions will contain an HMO or HMOs and comprise at least one of fat, protein, and carbohydrate.

Although total concentrations or amounts of the fat, protein, and carbohydrates may vary depending upon the product type (i.e., human milk fortifier, preterm infant formula, infant formula, etc.), product form (i.e., nutritional solid, powder, ready-to-feed liquid, concentrated liquid, or nutritional bar) and targeted dietary needs of the intended user, such concentrations or amounts most typically fall within one of the following embodied ranges, inclusive of any other essential fat, protein, and/or carbohydrate ingredients as described herein.

For the liquid formulas, carbohydrate concentrations most typically range from about 5% to about 40%, including from about 7% to about 30%, including from about 10% to about 25%, by weight; fat concentrations most typically range from about 1% to about 30%, including from about 2% to about 15%, and also including from about 3% to about 10%, by weight; and protein concentrations most typically range from about 0.5% to about 30%, including from about 1% to about 15%, and also including from about 2% to about 10%, by weight.

For the liquid human milk fortifier products, carbohydrate concentrations most typically range from about 10% to about 75%, including from about 10% to about 50%, including from about 20% to about 40%, by weight of the human milk fortifier; fat concentrations most typically range from about 10% to about 40%, including from about 15% to about 37%, and also including from about 18% to about 30%, by weight of the human milk fortifier; and protein concentrations most typically range from about 5% to about 40%, including from about 10% to about 30%, and also including from about 15% to about 25%, by weight of the human milk fortifier.

The amount of carbohydrates, fats, and/or proteins in any of the liquid nutritional compositions described herein may also be characterized in addition to, or in the alternative, as a percentage of total calories in the liquid nutritional composition as set forth in the following table. These macronutrients for liquid nutritional compositions used in the methods of the present disclosure are most typically formulated within any of the caloric ranges (embodiments A-F) described in the following table (each numerical value is preceded by the term "about").

TABLE 3

| Nutrient | Embodiment A (% Total Cal.) | Embodiment B (% Total Cal.) | Embodiment C (% Total Cal.) |
|---|---|---|---|
| Carbohydrate | 0-98 | 2-96 | 10-75 |
| Protein | 0-98 | 2-96 | 5-70 |
| Fat | 0-98 | 2-96 | 20-85 |

TABLE 4

| Nutrient | Embodiment D (% Total Cal.) | Embodiment E (% Total Cal.) | Embodiment F (% Total Cal.) |
|---|---|---|---|
| Carbohydrate | 30-50 | 25-50 | 25-50 |
| Protein | 15-35 | 10-30 | 5-30 |
| Fat | 35-55 | 1-20 | 2-20 |

In one specific example, liquid infant formulas (both ready-to-feed and concentrated liquids) include those embodiments in which the protein component may comprise from about 7.5% to about 25% of the caloric content of the formula; the carbohydrate component may comprise from about 35% to about 50% of the total caloric content of the infant formula; and the fat component may comprise from about 30% to about 60% of the total caloric content of the infant formula. These ranges are provided as examples only, and are not intended to be limiting. Additional suitable ranges are noted in the following table (each numerical value is preceded by the term "about").

TABLE 5

| Nutrient | Embodiment G (% Total Cal.) | Embodiment H (% Total Cal.) | Embodiment I (% Total Cal.) |
|---|---|---|---|
| Carbohydrates: | 20-85 | 30-60 | 35-55 |
| Fat: | 5-70 | 20-60 | 25-50 |
| Protein: | 2-75 | 5-50 | 7-40 |

When the nutritional product is a powdered adult, child, toddler, newborn, pediatric, preterm, or term infant formula, the protein component is present in an amount of from about 5% to about 35%, including from about 8% to about 12%, and including from about 10% to about 12% by weight of the preterm or term infant formula; the fat component is present in an amount of from about 10% to about 35%, including from about 25% to about 30%, and including from about 26% to about 28% by weight of the preterm or term infant formula; and the carbohydrate component is present in an amount of from about 30% to about 85%, including from about 45% to about 60%, including from about 50% to about 55% by weight of the preterm or term infant formula.

For powdered human milk fortifiers the protein component is present in an amount of from about 1% to about 55%, including from about 10% to about 50%, and including from about 10% to about 30% by weight of the human milk fortifier; the fat component is present in an amount of from about 1% to about 30%, including from about 1% to about 25%, and including from about 1% to about 20% by weight of the human milk fortifier; and the carbohydrate component is present in an amount of from about 15% to about 75%, including from about 15% to about 60%, including from about 20% to about 50% by weight of the human milk fortifier.

The total amount or concentration of fat, carbohydrate, and protein, in the powdered nutritional compositions used in the methods of the present disclosure can vary considerably depending upon the selected composition and dietary or medical needs of the intended user. Additional suitable examples of macronutrient concentrations are set forth below. In this context, the total amount or concentration refers to all fat, carbohydrate, and protein sources in the powdered product. For powdered nutritional compositions, such total amounts or concentrations are most typically and preferably formulated within any of the embodied ranges described in the following table (each numerical value is preceded by the term "about").

TABLE 6

| Nutrient | Embodiment J (% Total Cal.) | Embodiment K (% Total Cal.) | Embodiment L (% Total Cal.) |
|---|---|---|---|
| Carbohydrate | 1-85 | 30-60 | 35-55 |
| Fat | 5-70 | 20-60 | 25-50 |
| Protein | 2-75 | 5-50 | 7-40 |

When the nutritional product is a nutritional bar, the protein component is present in an amount of from about 5% to about 45%, including from about 15% to about 35%, and including from about 20% to about 30% by weight of the nutritional bar; the fat component is present in an amount of from about 2% to about 25%, including from about 5% to about 20%, and including from about 10% to about 15% by weight of the nutritional bar; and the carbohydrate component is present in an amount of from about 2% to about 25%, including from about 5% to about 20%, including from about 5% to about 15% by weight of the nutritional bar.

Fat

The nutritional compositions used in the methods of the present disclosure may comprise a source or sources of fat. Suitable additional sources of fat for use herein include any fat or fat source that is suitable for use in an oral nutritional product and is compatible with the essential elements and features of such products. For example, in one specific embodiment, the additional fat is derived from long chain polyunsaturated fatty acids and/or short chain fatty acids.

Additional non-limiting examples of suitable fats or sources thereof for use in the nutritional products described herein include coconut oil, fractionated coconut oil, soybean oil, corn oil, olive oil, safflower oil, high oleic safflower oil, oleic acids (EMERSOL 6313 OLEIC ACID, Cognis Oleochemicals, Malaysia), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof.

Protein

The nutritional compositions used in the methods of the present disclosure may further comprise protein. Any protein source that is suitable for use in oral nutritional compositions and is compatible with the essential elements and features of such products is suitable for use in the nutritional compositions.

Non-limiting examples of suitable proteins or sources thereof for use in the nutritional products include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy) or combinations thereof. Non-limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, and so forth. In one specific embodiment, the nutritional compositions include a protein source derived from milk proteins of human and/or bovine origin.

Carbohydrate

The nutritional products used in the methods of the present disclosure may further optionally comprise any carbohydrates that are suitable for use in an oral nutritional product and are compatible with the essential elements and features of such products.

Non-limiting examples of suitable carbohydrates or sources thereof for use in the nutritional products described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, *stevia*) and combinations thereof. A particularly desirable carbohydrate is a low dextrose equivalent (DE) maltodextrin.

Other Optional Ingredients

The nutritional compositions used in the methods of the present disclosure may further comprise other optional components that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, emulsifying agents, buffers, fructooligosaccharides, galactooligosaccharides, polydextrose, and other prebiotics (e.g., other neutral or acidic HMOs, inulin, oligofructose, polydextrose, pectin hydrolysate, and gums), probiotics (e.g., *B. animalis* subsp. *lactis* BB-12, *B. lactis* HNO19, *B. lactis* Bi07, *L. rhamnosus* GG, *L. rhamnosus* HNO01, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), postbiotics (metabolites of probiotics), long chain polyunsaturated fatty acids (DHA, ARA, DPA, EPA, etc.), nucleotides, antioxidant/anti-inflammatory compounds including tocopherols, caroteinoids, ascorbate/vitamin C, ascorbyl palmitate, polyphenols (e.g., curcumin), glutathione, and superoxide dismutase (melon), milk protein of human and/or bovine origin, soy protein, pea protein, other bioactive factors (e.g., growth hormones, cytokines, TFG-β) of human and/or bovine origin, tributyrin or other SCFA-containing mono-, di-, or triglylcerides, human milk-derived lipids, free amino acids or peptides (e.g., HMB, arginine, leucine, and/or glutamine), lactose, other water- and fat-soluble vitamins, minerals, and trace elements, pharmaceutical actives, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isomalt, and lactitol, and also preferably including at least one artificial or high potency sweetener such as acesulfame K, aspartame, sucralose, saccharin, *stevia*, and tagatose. These sweetening agents, especially as a combination of a sugar alcohol and an artificial sweetener, are especially useful in formulating liquid beverage embodiments of the present disclosure having a desirable favor profile. These sweetener combinations are especially effective in masking undesirable flavors sometimes associated with the addition of vegetable proteins to a liquid beverage. Optional sugar alcohol concentrations in the nutritional product may range from at least 0.01%, including from about 0.1% to about 10%, and also including from about 1% to about 6%, by weight of the nutritional product. Optional artificial sweetener concentrations may range from about 0.01%, including from about 0.05% to about 5%, also including from about 0.1% to about 1.0%, by weight of the nutritional product.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the nutritional composition.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

The nutritional compositions may further comprise any of a variety of other vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

Methods of Manufacture

The nutritional compositions used in the methods of the present disclosure may be prepared by any known or otherwise effective manufacturing technique for preparing the selected product solid or liquid form. Many such techniques are known for any given product form such as nutritional liquids, powders, and nutritional bars, and can easily be applied by one of ordinary skill in the art to the nutritional compositions described herein.

The nutritional compositions used in the methods of the present disclosure can therefore be prepared by any of a variety of known or otherwise effective formulation or manufacturing methods. In one suitable manufacturing process, for example, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., HMOs, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

The nutritional solid, such as a spray dried nutritional powder or drymixed nutritional powder, may be prepared by any collection of known or otherwise effective technique, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

The nutritional composition may be in the form of a bar. In one suitable manufacturing process, for example, the safflower oil, lecithin, glycerin, water, and flavors are added to a mixer. The dry powder ingredients and the vitamin mineral premix is added to the mixer and mixed for 1 minute. Corn syrup (heated to 95-105° F.) is added to the mixer and mixed for 2 minutes. Soy crisps and marshmallow bits are added to the mixer and mixed for 2 minutes. Chilled chocolate drops are added to the mixer and mixed for 1 minute. The mixture is formed into bars. A coating (preheated to 95-100° F.) is applied. Many different ingredients and mixing procedures may be used to make a nutritional bar.

Other suitable methods for making nutritional products are described, for example, in U.S. Pat. No. 6,365,218 (Borschel et al.), U.S. Pat. No. 6,589,576 (Borschel et al.), U.S. Pat. No. 6,306,908 (Carlson et al.), U.S. Patent Application 20030118703 A1 (Nguyen et al.), which descriptions are incorporated herein by reference to the extent that they are consistent herewith.

Product Form

The compositions used in the methods of the present disclosure may be formulated and administered in any known or otherwise suitable oral product form. Any solid, liquid, semi-solid, semi-liquid, or powder product form, including combinations or variations thereof, are suitable for use herein, provided that such forms allow for safe and effective oral delivery to the individual of the ingredients as also defined herein.

The compositions used in the methods of the present disclosure are desirably formulated as dietary product forms, which are defined herein as those embodiments comprising the ingredients of the present disclosure in a product form that then contains at least one of fat, protein, and carbohydrate, and preferably also contains vitamins, minerals, or combinations thereof.

The nutritional compositions may be formulated with sufficient kinds and amounts of nutrients to provide a sole, primary, or supplemental source of nutrition, or to provide a specialized nutritional product for use in individuals afflicted with specific conditions or with a targeted nutritional benefit as described below.

Some exemplary, non-limiting, examples of specific products that may be suitable for use in accordance with the present disclosure include preterm infant formulas, term infant formulas, human milk fortifiers, pediatric formulas, adult nutritional formulas, older adult nutritional formulas, medical formulas, geriatric nutritional formulas, diabetic nutritional formulas, nutritional bar, and the like.

Nutritional Liquids

Nutritional liquids include both concentrated and ready-to-feed nutritional liquids. These nutritional liquids are most typically formulated as suspensions or emulsions, although other liquid forms are within the scope of the present disclosure.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to 95% by weight of water, including from about 50% to 95%, also including from about 60% to about 90%, and also including from about 70% to about 85%, of water by weight of the nutritional emulsions. The nutritional emulsions may have a variety of product densities, but most typically have a density greater than 1.03 g/mL, including greater than 1.04 g/mL, including greater than 1.055 g/mL, including from about 1.06 g/mL to about 1.12 g/mL, and also including from about 1.085 g/mL to about 1.10 g/mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the emulsion may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least 1 mL, or even at least 2 mL, or even at least 5 mL, or even at least 10 mL, or even at least 25 mL, including ranges from 1 mL to about 300 mL, including from about 4 mL to about 250 mL, and including from about 10 mL to about 240 mL.

Nutritional Solids

The nutritional solids may be in any solid form but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

EXAMPLES

The exemplified compositions are shelf stable nutritional compositions prepared in accordance with the manufacturing methods described herein, such that each exemplified composition, unless otherwise specified, includes an aseptically processed embodiment and a retort packaged embodiment.

Examples 1-5

Prophetic examples 1-5 illustrate ready-to-feed nutritional emulsions, the ingredients of which are listed in the table below. All ingredient amounts listed are in kilograms, unless otherwise specified.

TABLE 7

Examples 1-5

| Ingredient | Ex. 1 | Ex. 2 | Ex. 3 | Ex. 4 | Ex. 5 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| lacto-N-neotetraose (LNnT) | 0.049 | 0.097 | 0.245 | 0.490 | 3.92 |
| Galactooligosaccharides (GOS) | 3.92 | 3.92 | 3.92 | 3.92 | 0 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, D3, E, K1 premix | 47.4 g | 47.4 g | 47.4 g | 47.4 g | 47.4 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 6-10

Prophetic examples 6-10 illustrate ready-to-feed nutritional emulsions of the present disclosure, the ingredients of which are listed in the table below. All ingredient amounts listed are in kilograms, unless otherwise specified.

TABLE 8

Examples 6-10

| Ingredient | Ex. 6 | Ex. 7 | Ex. 8 | Ex. 9 | Ex. 10 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 6' sialyllactose (6'SL) | 0.049 | 0.097 | 0.245 | 0.490 | 3.92 |
| Galactooligosaccharides (GOS) | 3.92 | 3.92 | 3.92 | 3.92 | 0 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, D3, E, K1 premix | 47.40 g | 47.40 g | 47.40 g | 47.40 g | 47.40 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 11-15

Prophetic examples 11-15 illustrate concentrated liquid emulsions, the ingredients of which are listed in the table below. All ingredient amounts listed are in kilograms, unless otherwise specified.

TABLE 9

Examples 11-15

| Ingredient | Ex. 11 | Ex. 12 | Ex. 13 | Ex. 14 | Ex. 15 |
|---|---|---|---|---|---|
| Water | Q.S. | Q.S. | Q.S. | Q.S. | Q.S. |
| Condensed Skim Milk | 157.67 | 157.67 | 157.67 | 157.67 | 157.67 |
| Lactose | 108.66 | 108.66 | 108.66 | 108.66 | 108.66 |
| High oleic safflower oil | 26.82 | 26.82 | 26.82 | 26.82 | 26.82 |
| Soybean oil | 20.16 | 20.16 | 20.16 | 20.16 | 20.16 |
| Coconut oil | 19.24 | 19.24 | 19.24 | 19.24 | 19.24 |
| 6' sialyllactose (6'SL) | 0.097 | 0.194 | 0.490 | 0.98 | 7.84 |
| Galactooligosaccharides (GOS) | 7.84 | 7.84 | 7.84 | 7.84 | 7.84 |
| Whey protein concentrate | 12.20 | 12.20 | 12.20 | 12.20 | 12.20 |
| Potassium citrate | 1.277 | 1.277 | 1.277 | 1.277 | 1.277 |
| Calcium carbonate | 996.1 g | 996.1 g | 996.1 g | 996.1 g | 996.1 g |
| Soy lecithin | 685.0 g | 685.0 g | 685.0 g | 685.0 g | 685.0 g |
| Monoglycerides | 685.0 g | 685.0 g | 685.0 g | 685.0 g | 685.0 g |
| ARA oil | 684.2 g | 684.2 g | 684.2 g | 684.2 g | 684.2 g |
| Nucleotide/chloride premix | 568.9 g | 568.9 g | 568.9 g | 568.9 g | 568.9 g |
| Potassium chloride | 429.7 g | 429.7 g | 429.7 g | 429.7 g | 429.7 g |
| Ascorbic acid | 293.8 g | 293.8 g | 293.8 g | 293.8 g | 293.8 g |
| Vitamin mineral premix | 276.9 g | 276.9 g | 276.9 g | 276.9 g | 276.9 g |
| DHA oil | 256.1 g | 256.1 g | 256.1 g | 256.1 g | 256.1 g |
| Carrageenan | 200.0 g | 200.0 g | 200.0 g | 200.0 g | 200.0 g |
| Magnesium chloride | 173.3 g | 173.3 g | 173.3 g | 173.3 g | 173.3 g |
| Ferrous sulfate | 112.7 g | 112.7 g | 112.7 g | 112.7 g | 112.7 g |
| Choline chloride | 104.8 g | 104.8 g | 104.8 g | 104.8 g | 104.8 g |
| Vitamin A, D3, E, K1 premix | 86.90 g | 86.90 g | 86.90 g | 86.90 g | 86.90 g |
| Citric acid | 57.50 g | 57.50 g | 57.50 g | 57.50 g | 57.50 g |
| Mixed carotenoid premix | 41.90 g | 41.90 g | 41.90 g | 41.90 g | 41.90 g |
| Sodium chloride | 23.50 g | 23.50 g | 23.50 g | 23.50 g | 23.50 g |
| L-carnitine | 6.40 g | 6.40 g | 6.40 g | 6.40 g | 6.40 g |
| Tricalcium phosphate | AN | AN | AN | AN | AN |
| Potassium phosphate monobasic | AN | AN | AN | AN | AN |
| Potassium hydroxide | AN | AN | AN | AN | AN |

AN = as needed

Examples 16-20

Prophetic examples 16-20 illustrate ready-to-feed nutritional emulsions, the ingredients of which are listed in the table below. All ingredient amounts listed are in kilograms, unless otherwise specified.

TABLE 10

Examples 16-20

| Ingredient | Ex. 16 | Ex. 17 | Ex. 18 | Ex. 19 | Ex. 20 |
| --- | --- | --- | --- | --- | --- |
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 6' sialyllactose (6'SL) | 0.049 | 0.097 | 0.245 | 0.490 | 0.98 |
| 2'fucosyllactose (2'FL) | 0.049 | 0.097 | 0.245 | 0.490 | 0.98 |
| Lacto-N-neotetraose (LNnT) | 0.049 | 0.097 | 0.245 | 0.490 | 0.98 |
| Galactooligosaccharides (GOS) | 3.92 | 3.92 | 3.92 | 1.96 | 0.98 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, D3, E, K1 premix | 47.40 g | 47.40 g | 47.40 g | 47.40 g | 47.40 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 21-25

Prophetic examples 21-25 illustrate concentrated liquid emulsions, the ingredients of which are listed in the table below. All ingredient amounts listed are in kilograms, unless otherwise specified.

TABLE 11

Examples 21-25

| Ingredient | Ex. 21 | Ex. 22 | Ex. 23 | Ex. 24 | Ex. 25 |
| --- | --- | --- | --- | --- | --- |
| Water | Q.S. | Q.S. | Q.S. | Q.S. | Q.S. |
| Condensed Skim Milk | 157.67 | 157.67 | 157.67 | 157.67 | 157.67 |
| Lactose | 108.66 | 108.66 | 108.66 | 108.66 | 108.66 |
| High oleic safflower oil | 26.82 | 26.82 | 26.82 | 26.82 | 26.82 |
| Soybean oil | 20.16 | 20.16 | 20.16 | 20.16 | 20.16 |
| Coconut oil | 19.24 | 19.24 | 19.24 | 19.24 | 19.24 |
| 6' sialyllactose (6'SL) | 0.097 | 0.194 | 0.490 | 0.98 | 1.96 |
| 2'fucosyllactose (2'FL) | 0.097 | 0.194 | 0.490 | 0.98 | 1.96 |
| Lacto-N-neotetraose (LNnT) | 0.097 | 0.194 | 0.490 | 0.98 | 1.96 |
| Galactooligosaccharides (GOS) | 7.84 | 7.84 | 7.84 | 3.92 | 3.921 |
| Whey protein concentrate | 12.20 | 12.20 | 12.20 | 12.20 | 12.20 |
| Potassium citrate | 1.277 | 1.277 | 1.277 | 1.277 | 1.277 |
| Calcium carbonate | 996.1 g | 996.1 g | 996.1 g | 996.1 g | 996.1 g |
| Soy lecithin | 685.0 g | 685.0 g | 685.0 g | 685.0 g | 685.0 g |
| Monoglycerides | 685.0 g | 685.0 g | 685.0 g | 685.0 g | 685.0 g |
| ARA oil | 684.2 g | 684.2 g | 684.2 g | 684.2 g | 684.2 g |
| Nucleotide/chloride premix | 568.9 g | 568.9 g | 568.9 g | 568.9 g | 568.9 g |
| Potassium chloride | 429.7 g | 429.7 g | 429.7 g | 429.7 g | 429.7 g |
| Ascorbic acid | 293.8 g | 293.8 g | 293.8 g | 293.8 g | 293.8 g |
| Vitamin mineral premix | 276.9 g | 276.9 g | 276.9 g | 276.9 g | 276.9 g |
| DHA oil | 256.1 g | 256.1 g | 256.1 g | 256.1 g | 256.1 g |
| Carrageenan | 200.0 g | 200.0 g | 200.0 g | 200.0 g | 200.0 g |
| Magnesium chloride | 173.3 g | 173.3 g | 173.3 g | 173.3 g | 173.3 g |
| Ferrous sulfate | 112.7 g | 112.7 g | 112.7 g | 112.7 g | 112.7 g |
| Choline chloride | 104.8 g | 104.8 g | 104.8 g | 104.8 g | 104.8 g |
| Vitamin A, D3, E, K1 premix | 86.90 g | 86.90 g | 86.90 g | 86.90 g | 86.90 g |
| Citric acid | 57.50 g | 57.50 g | 57.50 g | 57.50 g | 57.50 g |
| Mixed carotenoid premix | 41.90 g | 41.90 g | 41.90 g | 41.90 g | 41.90 g |
| Sodium chloride | 23.50 g | 23.50 g | 23.50 g | 23.50 g | 23.50 g |
| L-carnitine | 6.40 g | 6.40 g | 6.40 g | 6.40 g | 6.40 g |

TABLE 11-continued

Examples 21-25

| Ingredient | Ex. 21 | Ex. 22 | Ex. 23 | Ex. 24 | Ex. 25 |
|---|---|---|---|---|---|
| Tricalcium phosphate | AN | AN | AN | AN | AN |
| Potassium phosphate monobasic | AN | AN | AN | AN | AN |
| Potassium hydroxide | AN | AN | AN | AN | AN |

AN = as needed

Examples 26-30

Prophetic examples 26-30 illustrate human milk fortifier liquids, the ingredients of which are listed in the table below. All ingredient amounts listed are in kilograms, unless otherwise specified.

TABLE 12

Examples 26-30

| Ingredient | Ex. 26 | Ex. 27 | Ex. 28 | Ex. 29 | Ex. 30 |
|---|---|---|---|---|---|
| Water | Q.S. | Q.S. | Q.S. | Q.S. | Q.S. |
| Non-fat milk | 353 | 353 | 353 | 353 | 353 |
| Corn Syrup Solids | 85.3 | 85.3 | 85.3 | 85.3 | 85.3 |
| Medium Chain Triglycerides | 53.2 | 53.2 | 53.2 | 53.2 | 53.2 |
| Whey Protein Concentrate | 47.2 | 47.2 | 47.2 | 47.2 | 47.2 |
| 6' sialyllactose (6'SL) | 0.049 | 0.097 | 0.245 | 0.490 | 1.96 |
| 2'fucosyllactose (2'FL) | 0.049 | 0.097 | 0.245 | 0.490 | 1.96 |
| Lacto-N-neotetraose (LNnT) | 0.049 | 0.097 | 0.245 | 0.490 | 1.96 |
| Calcium Phosphate | 25.5 | 25.5 | 25.5 | 25.5 | 25.5 |
| Ascorbic Acid | 5.6 | 5.6 | 5.6 | 5.6 | 5.6 |
| Potassium Citrate | 3.1 | 3.1 | 3.1 | 3.1 | 3.1 |
| Magnesium Chloride | 2.8 | 2.8 | 2.8 | 2.8 | 2.8 |
| Sodium Citrate | 1.4 | 1.4 | 1.4 | 1.4 | 1.4 |
| Sodium Chloride | 1.4 | 1.4 | 1.4 | 1.4 | 1.4 |
| Soy Lecithin | 609 g | 609 g | 609 g | 609 g | 609 g |
| M-Inositol | 500 g | 500 g | 500 g | 500 g | 500 g |
| Niacinamide | 400 g | 400 g | 400 g | 400 g | 400 g |
| ARA Oil | 313 g | 313 g | 313 g | 313 g | 313 g |
| Tocopherol Acetate | 310 g | 310 g | 310 g | 310 g | 310 g |
| Zinc Sulfate | 300 g | 300 g | 300 g | 300 g | 300 g |
| Calcium Pantothenate | 182 g | 182 g | 182 g | 182 g | 182 g |
| Ferrous Sulfate | 133 g | 133 g | 133 g | 133 g | 133 g |
| DHA Oil | 116 g | 116 g | 116 g | 116 g | 116 g |
| Vitamin A Palmitate | 100 g | 100 g | 100 g | 100 g | 100 g |
| Cupric Sulfate | 51.0 g | 51.0 g | 51.0 g | 51.0 g | 51.0 g |
| Thiamine Hydrochloride | 50.0 g | 50.0 g | 50.0 g | 50.0 g | 50.0 g |
| Riboflavin | 47.0 g | 47.0 g | 47.0 g | 47.0 g | 47.0 g |
| Pyridoxine Hydrochloride | 27.0 g | 27.0 g | 27.0 g | 27.0 g | 27.0 g |
| Vitamin D3 | 20.0 g | 20.0 g | 20.0 g | 20.0 g | 20.0 g |
| Folic Acid | 3.5 g | 3.5 g | 3.5 g | 3.5 g | 3.5 g |
| Biotin | 3.4 g | 3.4 g | 3.4 g | 3.4 g | 3.4 g |
| Manganous Sulfate | 1.5 g | 1.5 g | 1.5 g | 1.5 g | 1.5 g |
| Phylloquinone | 1.2 g | 1.2 g | 1.2 g | 1.2 g | 1.2 g |
| Cyanocobalamin | 100 mg | 100 mg | 100 mg | 100 mg | 100 mg |
| Sodium Selenate | 43.0 mg | 43.0 mg | 43.0 mg | 43.0 mg | 43.0 mg |

Examples 31-35

Prophetic examples 31-35 illustrate spray dried nutritional powders, the ingredients of which are listed in the table below. All ingredient amounts listed are in kilograms, unless otherwise specified.

TABLE 13

Examples 31-35

| Ingredient | Ex. 31 | Ex. 32 | Ex. 33 | Ex. 34 | Ex. 35 |
|---|---|---|---|---|---|
| Condensed Skim Milk | 698.5 | 698.5 | 698.5 | 698.5 | 698.5 |
| Lactose | 386.0 | 386.0 | 386.0 | 386.0 | 386.0 |
| High oleic safflower oil | 114.4 | 114.4 | 114.4 | 114.4 | 114.4 |
| Soybean oil | 85.51 | 85.51 | 85.51 | 85.51 | 85.51 |
| Coconut oil | 78.76 | 78.76 | 78.76 | 78.76 | 78.76 |
| Lacto-N-neotetraose (LNnT) | 0.385 | 0.770 | 1.925 | 3.85 | 30.8 |
| Galactooligosaccharides (GOS) | 30.8 | 30.8 | 30.8 | 30.8 | 0 |
| Whey protein concentrate | 51.08 | 51.08 | 51.08 | 51.08 | 51.08 |
| Potassium citrate | 9.168 | 9.168 | 9.168 | 9.168 | 9.168 |
| Calcium carbonate | 4.054 | 4.054 | 4.054 | 4.054 | 4.054 |
| Soy lecithin | 1.120 | 1.120 | 1.120 | 1.120 | 1.120 |
| ARA oil | 2.949 | 2.949 | 2.949 | 2.949 | 2.949 |
| Nucleotide/chloride premix | 2.347 | 2.347 | 2.347 | 2.347 | 2.347 |
| Potassium chloride | 1.295 | 1.295 | 1.295 | 1.295 | 1.295 |
| Ascorbic acid | 1.275 | 1.275 | 1.275 | 1.275 | 1.275 |
| Vitamin mineral premix | 1.116 | 1.116 | 1.116 | 1.116 | 1.116 |
| DHA oil | 1.113 | 1.113 | 1.113 | 1.113 | 1.113 |
| Magnesium chloride | 1.038 | 1.038 | 1.038 | 1.038 | 1.038 |
| Sodium chloride | 579.4 g | 579.4 g | 579.4 g | 579.4 g | 579.4 g |
| Ferrous sulfate | 453.6 g | 453.6 g | 453.6 g | 453.6 g | 453.6 g |

TABLE 13-continued

Examples 31-35

| Ingredient | Ex. 31 | Ex. 32 | Ex. 33 | Ex. 34 | Ex. 35 |
|---|---|---|---|---|---|
| Choline chloride | 432.1 g | 432.1 g | 432.1 g | 432.1 g | 432.1 g |
| Vitamin A, D3, E, K1 premix | 377.2 g | 377.2 g | 377.2 g | 377.2 g | 377.2 g |
| Ascorbyl Palmitate | 361.3 g | 361.3 g | 361.3 g | 361.3 g | 361.3 g |
| Mixed carotenoid premix | 350.1 g | 350.1 g | 350.1 g | 350.1 g | 350.1 g |
| Mixed Tocopherols | 159.2 g | 159.2 g | 159.2 g | 159.2 g | 159.2 g |
| L-carnitine | 26.30 g | 26.30 g | 26.30 g | 26.30 g | 26.30 g |
| Riboflavin | 3.181 g | 3.181 g | 3.181 g | 3.181 g | 3.181 g |
| Tricalcium phosphate | 0-5.23 | 0-5.23 | 0-5.23 | 0-5.23 | 0-5.23 |
| Potassium phosphate monobasic | 0-5.23 | 0-5.23 | 0-5.23 | 0-5.23 | 0-5.23 |
| Potassium hydroxide | AN | AN | AN | AN | AN |

AN = as needed

Examples 36-40

Prophetic examples 36-40 illustrate nutritional bars, the ingredients of which are listed in the table below. All ingredient amounts listed are in kilograms, unless otherwise specified.

TABLE 14

Examples 36-40

| Ingredient | Ex. 36 | Ex. 37 | Ex. 38 | Ex. 39 | Ex. 40 |
|---|---|---|---|---|---|
| Soy Crisps | 298.80 | 298.80 | 298.80 | 298.80 | 298.80 |
| Coating, Dark Chocolate | 196.90 | 196.90 | 196.90 | 196.90 | 196.90 |
| Corn Syrup | 177.90 | 177.90 | 177.90 | 177.90 | 177.90 |
| Milk Chocolate Drops | 54.80 | 54.80 | 54.80 | 54.80 | 54.80 |
| Marshmallow | 51.00 | 51.00 | 51.00 | 51.00 | 51.00 |
| Fructooligosaccharide Powder | 50.10 | 50.10 | 50.10 | 50.10 | 50.10 |
| Milk Protein Isolate Fonterra | 50.00 | 50.00 | 50.00 | 50.00 | 50.00 |
| High Oleic Sunflower Oil or High Oleic Safflower Oil | 32.40 | 32.40 | 32.40 | 32.40 | 32.40 |
| Glycerine | 23.20 | 23.20 | 23.20 | 23.20 | 23.20 |
| Corn Syrup | 18.00 | 18.00 | 18.00 | 18.00 | 18.00 |
| Crystalline Fructose | 14.70 | 14.70 | 14.70 | 14.70 | 14.70 |
| Vitamin/Mineral Premix | 13.20 | 13.20 | 13.20 | 13.20 | 13.20 |
| Flavor | 7.60 | 7.60 | 7.60 | 7.60 | 7.60 |
| Tricalcium Phosphate | 5.10 | 5.10 | 5.10 | 5.10 | 5.10 |
| Water | 3.50 | 3.50 | 3.50 | 3.50 | 3.50 |
| Flavor, Vanilla Natural | 1.00 | 1.00 | 1.00 | 1.00 | 1.00 |
| Xanthan Gum | 0.80 | 0.80 | 0.80 | 0.80 | 0.80 |
| MagNifique Glycerrhizinate | 0.70 | 0.70 | 0.70 | 0.70 | 0.70 |
| Soy Lecithin | 0.30 | 0.30 | 0.30 | 0.30 | 0.30 |
| lacto-N-neotetraose (LNnT) | 1.00 | 2.00 | 5.00 | 10.00 | 80.00 |

Examples 41-45

Prophetic examples 41-45 illustrate liquid formulations, the ingredients of which are listed in the table below. All ingredient amounts listed are in kilograms, unless otherwise specified.

TABLE 15

Examples 41-45

| Ingredient | Ex. 41 | Ex. 42 | Ex. 43 | Ex. 44 | Ex. 45 |
|---|---|---|---|---|---|
| Water | Q.S. | Q.S. | Q.S. | Q.S. | Q.S. |
| Fibersol 2 | 57.3 | 57.3 | 57.3 | 57.3 | 57.3 |
| Sucromalt | 29.1 | 29.1 | 29.1 | 29.1 | 29.1 |
| Acid Casein | 27.3 | 27.3 | 27.3 | 27.3 | 27.3 |
| Glycerine | 15.0 | 15.0 | 15.0 | 15.0 | 15.0 |
| Soy Protein Isolate | 14.1 | 14.1 | 14.1 | 14.1 | 14.1 |
| Fructose | 10.8 | 10.8 | 10.8 | 10.8 | 10.8 |
| High Oleic Safflower Oil | 10.8 | 10.8 | 10.8 | 10.8 | 10.8 |
| Canola Oil | 8.1 | 8.1 | 8.1 | 8.1 | 8.1 |
| Soy Oil | 6.8 | 6.8 | 6.8 | 6.8 | 6.8 |
| Calcium Caseinate | 4.4 | 4.4 | 4.4 | 4.4 | 4.4 |
| Maltrin M100 | 4.2 | 4.2 | 4.2 | 4.2 | 4.2 |
| 20% Potassium Citrate | 3.3 | 3.3 | 3.3 | 3.3 | 3.3 |
| Potassium Citrate | 661.6 g | 661.6 g | 661.6 g | 661.6 g | 661.6 g |
| Plant Sterol Esters | 3.2 | 3.2 | 3.2 | 3.2 | 3.2 |
| 20% Sodium Hydroxide | 2.9 | 2.9 | 2.9 | 2.9 | 2.9 |
| Calcium Phosphate | 2.8 | 2.8 | 2.8 | 2.8 | 2.8 |
| Magnesium Chloride | 2.4 | 2.4 | 2.4 | 2.4 | 2.4 |
| French Vanilla flavoring | 2.3 | 2.3 | 2.3 | 2.3 | 2.3 |
| Sodium Citrate | 1.5 | 1.5 | 1.5 | 1.5 | 1.5 |
| Soy Lecithin | 1.4 | 1.4 | 1.4 | 1.4 | 1.4 |
| Magnesium Phosphate | 1.0 | 1.0 | 1.0 | 1.0 | 1.0 |
| Artificial Vanilla | 1.0 | 1.0 | 1.0 | 1.0 | 1.0 |
| Potassium Chloride | 850.0 g | 850.0 g | 850.0 g | 850.0 g | 850.0 g |
| Potassium Phosphate | 800.0 g | 800.0 g | 800.0 g | 800.0 g | 800.0 g |
| Potassium Citrate | 688.4 g | 688.4 g | 688.4 g | 688.4 g | 688.4 g |
| Choline Chloride | 651.5 g | 651.5 g | 651.5 g | 651.5 g | 651.5 g |
| Ascorbic Acid | 584.1 g | 584.1 g | 584.1 g | 584.1 g | 584.1 g |
| Carrageenan | 500.0 g | 500.0 g | 500.0 g | 500.0 g | 500.0 g |
| 45% Potassium Hydroxide | 418.1 g | 418.1 g | 418.1 g | 418.1 g | 418.1 g |
| Ferrous Sulfate, Dried | 61.5 g | 61.5 g | 61.5 g | 61.5 g | 61.5 g |
| Zinc Sulfate, Monohydrate | 48.4 g | 48.4 g | 48.4 g | 48.4 g | 48.4 g |
| Niacinamide | 25.5 g | 25.5 g | 25.5 g | 25.5 g | 25.5 g |

TABLE 15-continued

| | Examples 41-45 | | | | |
|---|---|---|---|---|---|
| Ingredient | Ex. 41 | Ex. 42 | Ex. 43 | Ex. 44 | Ex. 45 |
| Calcium Pantothenate | 18.1 g | 18.1 g | 18.1 g | 18.1 g | 18.1 g |
| Chromium Picolinate, Anhydrous | 8.3 g | 8.3 g | 8.3 g | 8.3 g | 8.3 g |
| Manganese Sulfate, Monohydrate | 7.7 g | 7.7 g | 7.7 g | 7.7 g | 7.7 g |
| Cupric Sulfate, Anhydrous | 6.0 g | 6.0 g | 6.0 g | 6.0 g | 6.0 g |
| Pyridoxine Hydrochloride | 4.2 g | 4.2 g | 4.2 g | 4.2 g | 4.2 g |
| Thiamine Chloride Hydrochloride | 4.0 g | 4.0 g | 4.0 g | 4.0 g | 4.0 g |
| Riboflavin | 3.0 g | 3.0 g | 3.0 g | 3.0 g | 3.0 g |
| Folic Acid | 623.6 mg | 623.6 mg | 623.6 mg | 623.6 mg | 623.6 mg |
| Biotin | 476.5 mg | 476.5 mg | 476.5 mg | 476.5 mg | 476.5 mg |
| Sodium Molybdate, Dihydrate | 247.2 mg | 247.2 mg | 247.2 mg | 247.2 mg | 247.2 mg |
| Sodium Selenate, Anhydrous | 211.5 mg | 211.5 mg | 211.5 mg | 211.5 mg | 211.5 mg |
| Cyanocobalamin | 12.5 mg | 12.5 mg | 12.5 mg | 12.5 mg | 12.5 mg |
| Sucralose | 33.0 g | 33.0 g | 33.0 g | 33.0 g | 33.0 g |
| Acesulfame Potassium | 76.0 g | 76.0 g | 76.0 g | 76.0 g | 76.0 g |
| dl-Alpha-Tocopheryl Acetate | 54.5 g | 54.5 g | 54.5 g | 54.5 g | 54.5 g |
| Phylloquinone | 92.4 mg | 92.4 mg | 92.4 mg | 92.4 mg | 92.4 mg |
| Vitamin D3 | 13.2 mg | 13.2 mg | 13.2 mg | 13.2 mg | 13.2 mg |
| Vitamin A Palmitate | 4.5 g | 4.5 g | 4.5 g | 4.5 g | 4.5 g |
| Potassium Iodide | 220.5 mg | 220.5 mg | 220.5 mg | 220.5 mg | 220.5 mg |
| Vitamin B12 (86.4% Cyanocobalamin) | 31.7 mg | 31.7 mg | 31.7 mg | 31.7 mg | 31.7 mg |
| lacto-N-neotetraose (LNnT) | 0.392 | 1.96 | 3.92 | 7.84 | 15.68 |

Examples 46-50

Prophetic examples 46-50 illustrate liquid formulations, the ingredients of which are listed in the table below. All ingredient amounts listed are in kilograms, unless otherwise specified.

TABLE 16

| | Examples 46-50 | | | | |
|---|---|---|---|---|---|
| Ingredient | Ex. 46 | Ex. 47 | Ex. 48 | Ex. 49 | Ex. 50 |
| Water | Q.S. | Q.S. | Q.S. | Q.S. | Q.S. |
| Sugar | 87.7 | 87.7 | 87.7 | 87.7 | 87.7 |
| Corn maltodextrin | 70.7 | 70.7 | 70.7 | 70.7 | 70.7 |
| Milk protein concentrate | 26.2 | 26.2 | 26.2 | 26.2 | 26.2 |
| Soy oil | 13.4 | 13.4 | 13.4 | 13.4 | 13.4 |
| Soy protein isolate | 10.5 | 10.5 | 10.5 | 10.5 | 10.5 |
| Pea protein concentrate | 6.2 | 6.2 | 6.2 | 6.2 | 6.2 |
| Canola oil | 5.4 | 5.4 | 5.4 | 5.4 | 5.4 |
| Corn oil | 4.1 | 4.1 | 4.1 | 4.1 | 4.1 |
| Magnesium phosphate | 2.9 | 2.9 | 2.9 | 2.9 | 2.9 |
| Potassium citrate | 2.1 | 2.1 | 2.1 | 2.1 | 2.1 |
| Cellulosegel | 2.0 | 2.0 | 2.0 | 2.0 | 2.0 |
| Natural and artificial flavor | 2.0 | 2.0 | 2.0 | 2.0 | 2.0 |
| Calcium carbonate | 1.0 | 1.0 | 1.0 | 1.0 | 1.0 |
| Potassium chloride | 1.0 | 1.0 | 1.0 | 1.0 | 1.0 |
| Calcium phosphate | 960.0 g | 960.0 g | 960.0 g | 960.0 g | 960.0 g |
| Sodium citrate | 800.0 g | 800.0 g | 800.0 g | 800.0 g | 800.0 g |
| Salt | 710.0 g | 710.0 g | 710.0 g | 710.0 g | 710.0 g |
| Choline chloride | 480.0 g | 480.0 g | 480.0 g | 480.0 g | 480.0 g |
| Ascorbic acid | 468.7 g | 468.7 g | 468.7 g | 468.7 g | 468.7 g |
| Cellulosegum | 360.0 g | 360.0 g | 360.0 g | 360.0 g | 360.0 g |
| Monoglycerides | 286.6 g | 286.6 g | 286.6 g | 286.6 g | 286.6 g |
| Soy lecithin | 286.6 g | 286.6 g | 286.6 g | 286.6 g | 286.6 g |
| Carrageenan | 240.0 g | 240.0 g | 240.0 g | 240.0 g | 240.0 g |
| Potassium hydroxide | 145.4 g | 145.4 g | 145.4 g | 145.4 g | 145.4 g |
| Ferrous sulfate | 59.8 g | 59.8 g | 59.8 g | 59.8 g | 59.8 g |
| dl-alpha-tocopheryl acetate | 54.8 g | 54.8 g | 54.8 g | 54.8 g | 54.8 g |
| Zinc sulfate | 45.6 g | 45.6 g | 45.6 g | 45.6 g | 45.6 g |
| Niacinamide | 25.9 g | 25.9 g | 25.9 g | 25.9 g | 25.9 g |
| Manganese sulfate | 17.6 g | 17.6 g | 17.6 g | 17.6 g | 17.6 g |
| Calcium pantothenate | 16.7 g | 16.7 g | 16.7 g | 16.7 g | 16.7 g |
| Cupric sulfate | 9.2 g | 9.2 g | 9.2 g | 9.2 g | 9.2 g |
| Vitamin A palmitate | 4.3 g | 4.3 g | 4.3 g | 4.3 g | 4.3 g |
| Thiamine chloride hydrochloride | 4.3 g | 4.3 g | 4.3 g | 4.3 g | 4.3 g |
| Pyridoxine hydrochloride | 4.1 g | 4.1 g | 4.1 g | 4.1 g | 4.1 g |
| Riboflavin | 3.3 g | 3.3 g | 3.3 g | 3.3 g | 3.3 g |
| Folic acid | 580.0 mg | 580.0 mg | 580.0 mg | 580.0 mg | 580.0 mg |

TABLE 16-continued

Examples 46-50

| Ingredient | Ex. 46 | Ex. 47 | Ex. 48 | Ex. 49 | Ex. 50 |
|---|---|---|---|---|---|
| Chromium chloride | 561.0 mg | 561.0 mg | 561.0 mg | 561.0 mg | 561.0 mg |
| Biotin | 504.0 mg | 504.0 mg | 504.0 mg | 504.0 mg | 504.0 mg |
| Sodium molybdate | 441.0 mg | 441.0 mg | 441.0 mg | 441.0 mg | 441.0 mg |
| Potassium iodide | 207.0 mg | 207.0 mg | 207.0 mg | 207.0 mg | 207.0 mg |
| Sodium selenate | 195.0 mg | 195.0 mg | 195.0 mg | 195.0 mg | 195.0 mg |
| Phylloquinone | 81.3 mg | 81.3 mg | 81.3 mg | 81.3 mg | 81.3 mg |
| Vitamin D3 | 13.3 mg | 13.3 mg | 13.3 mg | 13.3 mg | 13.3 mg |
| Cyanocobalamin | 11.4 mg | 11.4 mg | 11.4 mg | 11.4 mg | 11.4 mg |
| lacto-N-neotetraose (LNnT) | 0.392 | 1.96 | 3.92 | 7.84 | 15.68 |

Example 51

Fecal samples from eight human babies, one group of four breast-fed and the other group of four formula-fed, were used as inocula for anaerobic fermentation (37° C.) of lacto-N-neotetraose (LNnT) and 6'-sialyllactose. Supernatants from the fermentation cultures were sampled at 0 hr, 3 hr, and 6 hr. A culture without addition of HMOs served as a control. A sample of the fermentation medium (blank), which constituted approximately 90% of the starting culture volume, was also analyzed.

Samples were extracted and split into equal parts for analysis on GC/MS and LC/MS/MS platforms. GABA and agmatine ions were identified in chromatograms, and peak area was integrated for quantitative analysis. The resulting data in tables 1 and 2 shows the relative ratios of GABA and agmatine compared to the blank for both breast fed and formula fed infants.

While the present disclosure has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

What is claimed is:

1. A method of reducing psychological stress in an individual in need thereof, comprising administering a synthetic nutritional composition comprising at least one human milk oligosaccharide, the at least one human milk oligosaccharide selected from the group consisting of 6'-sialyllactose, lacto-N-neotetraose, and combinations thereof, wherein the synthetic nutritional composition does not comprise any other human milk oligosaccharides, and wherein administration of the synthetic nutritional composition increases at least one of gamma aminobutyric acid and agmatine and thereby reduces psychological stress in the individual.

2. The method of claim 1, wherein the at least one human milk oligosaccharide is lacto-N-neotetraose.

3. The method of claim 1, wherein the at least one human milk oligosaccharide is 6'-sialyllactose.

4. The method of claim 1, wherein the nutritional composition is a liquid and comprises from about 0.001 mg/mL to about 20 mg/mL of the at least one human milk oligosaccharide.

5. The method of claim 1, wherein the nutritional composition is a liquid and comprises from about 0.001 mg/mL to about 5 mg/mL of the at least one human milk oligosaccharide.

6. The method of claim 1, wherein the nutritional composition is a powder and comprises from about 0.01% to about 1% of the at least one human milk oligosaccharide, by weight of the powder.

7. The method of claim 1, wherein the nutritional composition further comprises at least one of fat, protein, or carbohydrate.

8. The method of claim 7, wherein the nutritional composition comprises protein.

9. The method of claim 8, wherein the nutritional composition is an infant formula.

10. The method of claim 7, wherein the nutritional composition is a nutritional bar, liquid, or powder.

11. A method of increasing a level of at least one of gamma aminobutyric acid and agmatine, in an individual in need thereof, comprising administering a synthetic nutritional composition comprising at least one human milk oligosaccharide, the at least one human milk oligosaccharide selected from the group consisting of 6'-sialyllactose, lacto-N-neotetraose, and combinations thereof, wherein the synthetic nutritional composition does not comprise any other human milk oligosaccharides, and wherein increasing the level of at least one of gamma aminobutyric acid and agmatine reduces psychological stress in the individual.

* * * * *